United States Patent
Miao

(10) Patent No.: US 10,107,815 B2
(45) Date of Patent: Oct. 23, 2018

(54) MICROPLATE AND IN VITRO DIAGNOSTIC KIT FOR HPV 16/E7 ONCOPROTEIN DETECTION AND PREPARATION METHOD THEREOF

(71) Applicant: Jinchao Miao, Tianjin (CN)

(72) Inventor: Jinchao Miao, Tianjin (CN)

( * ) Notice: Subject to any disclaimer, the term of this patent is extended or adjusted under 35 U.S.C. 154(b) by 0 days.

(21) Appl. No.: 15/497,228

(22) Filed: Apr. 26, 2017

(65) Prior Publication Data

US 2017/0285031 A1    Oct. 5, 2017

(30) Foreign Application Priority Data

Feb. 26, 2016    (CN) .......................... 2016 1 0107596

(51) Int. Cl.
*G01N 33/574*    (2006.01)
*G01N 33/543*    (2006.01)

(52) U.S. Cl.
CPC . *G01N 33/57411* (2013.01); *G01N 33/54366* (2013.01); *G01N 33/5748* (2013.01)

(58) Field of Classification Search
None
See application file for complete search history.

(56) References Cited

U.S. PATENT DOCUMENTS 8,021,695 B2 * 9/2011 Gruber ................. A61K 8/068
                                                              424/725
9,249,212 B2 * 2/2016 Jansen-Durr ........ C07K 16/084

OTHER PUBLICATIONS

Ehehalt et al. Detection of Human Papillomavirus Type 18 E7 Oncoprotein in Cervical Smears: a Feasibility Study. Journal of Clinical Microbiology. 2012. 50: 246-257.*
Tsitsilonis et al. Serological detection of hepatitis B viral infection by a panel of solid-phase enzyme-linked immunosorbent assays (ELISA). Journal of Pharmaceutical and Biomedical Analysis. 2004. 34: 811-822.*
Yucel et al. Production and Characterization of Monoclonal Antibodies Against Hepatitis B Viruses and Application of a Quick Sandwich ELISA. Hybridoma and Hybridomics. 2003. 22: 173-177.*
BD Bioscience. ELISA: Frequently Asked Questions. Sep. 2010. pp. 1-4. https://www.bdbiosciences.com/documents/ELISA_FAQ.pdf.*
Protocol Online. Non-specific binding in ELISA assays—Reducing background with human serum (Sep. 23, 2003 ). pp. 1-2.*
Demerdash et al. Diagnostic efficacy of monoclonal antibody based sandwich enzyme linked immunosorbent assay (ELISA) for detection of Fasciola gigantica excretory/secretory antigens in both serum and stool Parasites & Vectors 2011, 4:176.*

* cited by examiner

*Primary Examiner* — Nianxiang Zou
(74) *Attorney, Agent, or Firm* — JCIPRNET

(57) ABSTRACT

The invention relates to a microplate, an in vitro diagnostic kit for HPV type 16 E7 oncoprotein detection and a preparation method thereof. The in vitro diagnostic kit is comprised of a microplate pre-coated with an HPV type 16 E7 antibody and an HRP-labeled HPV type 16 E7 antibody with concentration of 0.05-0.4 µg/ml, wherein the amount of the antibody in each microwell of the microplate is 0.05-0.5 µg. The in vitro diagnostic kit is used for directly detecting the expression of high-risk HPV-associated oncoprotein and the expression level, and thus has a clear judgment on the infection degree of high-risk HPV, and facilitates subsequent treatment.

3 Claims, 1 Drawing Sheet

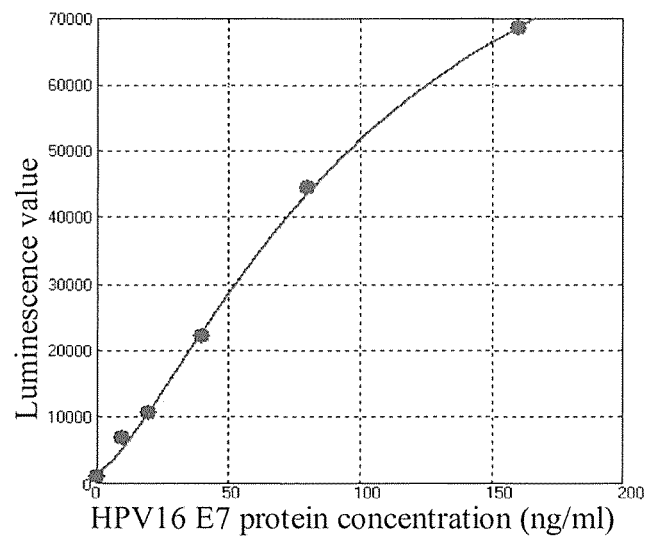

MICROPLATE AND IN VITRO DIAGNOSTIC KIT FOR HPV 16/E7 ONCOPROTEIN DETECTION AND PREPARATION METHOD THEREOF

CROSS-REFERENCE TO RELATED APPLICATION

This application claims the priority benefit of China application serial no. 201610107596.4, filed on Feb. 26, 2016. The entirety of the above-mentioned patent application is hereby incorporated by reference herein and made a part of this specification.

BACKGROUND OF THE INVENTION

Technical Field

The invention relates to a microplate and an in vitro diagnostic kit, in particular to a microplate and an in vitro diagnostic kit for the HPV type 16 E7 oncoprotein detection.

Description of Related Art

Cervical cancer is the second most common cancer diagnosis in women, and is associated with high-risk human papillomavirus (HPV) infection in the cases of 99.7%. In the world, there are about 400,000 new cases of cervical cancer, and nearly 200,000 dead cases each year. (There are more than 100 HPV types) that have been broadly divided into high-risk and low-risk subtypes according to their association with cervical cancer or with benign cervical lesions or atypical hyperplasia. Low-risk HPV, including HPV6, 11, 42, 43, 44, etc., often causes external genital warts and other benign lesions, including cervical intraepithelial neoplasia I (CIN I). High-risk HPV, including HPV16, 18, 31, 33, 35, 39, 45, 51, 52, 56, 58, 59, 68, CP8304 and other subtypes, is associated with cervical cancer and cervical intraepithelial neoplasia II/III (CIN II/III), especially HPV16 and 18 types, of which HPV16 accounts for more than or equal to 50%.

The human papilloma virus (HPV) is a double-stranded DNA virus that infects the epithelial cells of skin and mucosa. The HPV genome is divided into three main regions, early region (E region), late region (L region) and uncoding region (UCR) or upstream regulatory region (URR). The E region includes seven genes of E6, E7, E1, E2, E3, E4 and E5 in sequence, which are involved in viral DNA replication and transcription. protein coding, and maintaining the high copy number of the intracellular virus. Among them, E6 and E7 are the major oncogenes of HPV, and are associated with the virus cell transformation function and carcinogenicity. E6 and E7 proteins inactivate tumor suppressor proteins p53 and pRB to respectively deregulate cell cycle control and inhibit apoptosis. Thus, the best way to determine the HPV status in a tumor is to measure the E6/E7 proteins in tumor cells.

At present, the main detection methods of human papillomavirus (HPV) include in-situ hybridization, DNA direct capture and various PCR methods. The real-time fluorescence quantitative PCR technology, which is based on the traditional PCR of the mid 1990s, has transformed from the old qualitative detection to the new quantitative detection, and has become an important tool in molecular diagnostic research with its specificity, high sensitivity, good reproducibility, quantitative accuracy, high speed, full-closed reaction and other advantages.

However, the above method is only capable of detecting the infection of human papillomavirus (HPV) on the gene level, the real-time fluorescence quantitative PCR technique cannot give an accurate judgment on the expression of oncoprotein, and needs real-time fluorescence quantitative PCR instrument, thereby being high in detection costs.

BRIEF SUMMARY OF THE INVENTION

This invention aims to overcome the shortcomings of the prior art, and provides a chemiluminescent in vitro diagnostic kit for detection of high-risk human papillomavirus (HPV) type 16 E7 oncoprotein. Lysed cervical cells are directly added to detect the expression levels of high-risk HPV-associated oncoprotein thus a clear judgment on the infection degree of high-risk HPV is achieved, and subsequent treatment is facilitated, with which the current detection methods (including real-time fluorescence quantitative PCR technique) cannot be comparable.

The kit of the invention adopts the double-antibody sandwich method and uses the antibody to detect the high-risk HPV type 16 E7 oncoprotein in human cervical exfoliated cells. The cervical exfoliated cells are lysed and directly added into the microplate coated with the specific antibody, after incubation and washing, the HRP-labeled antibody is added, and then the substrate is added after incubation and washing. The luminescence value is measured by a chemiluminescence reader. The luminescence signal is positively correlated with the E7 oncoprotein concentration in samples, thus the quantitative detection of the HPV type 16 E7 oncoprotein in human cervical exfoliated cells is established.

The following technical schemes are adopted by the invention.

The invention provides a microplate for HPV type 16 E7 oncoprotein detection, and the microplate is pre-coated with an HPV type 16 E7 antibody.

Preferably, the coating amount of the antibody in each microwell of the microplate is 0.05-0.5 µg.

Preferably, a method for preparing the microplate includes the following steps of taking an HPV type 16 E7 antibody, adding a coating buffer to the wells at an amount of 100 µl/well and standing at 4° C. overnight (16-18 h); washing the microwells with washing solution five times at an amount of 300 µl/well; adding a blocking solution to the wells at an amount of 300 µl/well, and standing at 37° C. for 1-2 h for blocking; suction-drying in a drying room (18-26° C.) and sealing in vacuum (2-8° C.) to obtain a microwell plate coated with the HPV type 16 E7 antibody, and drying and storing, wherein the coating buffer is prepared by adding 0.5-5 mg of antibody to 1000 ml of buffer, and the buffer includes 1.59 g/L of $Na_2CO_3$ and 2.93 g/L of $NaHCO_3$; the washing solution includes 1.44 g/L of $Na_2HPO_4$, 0.24 g/L of $KH_2PO_4$, 8 g/L of NaCl, 0.2 g/L of KCl, 0.5 ml/L of Tween-20, and 0.3 ml/L of Proclin 300; and the blocking solution includes 1.44 g/L of $Na_2HPO_4$, 0.24 g/L of $KH_2PO_4$, 8 g/L of NaCl, 0.2 g/L of KCl, 10 g/L of BAS, 25 g/L of sucrose and 0.3 ml/L of Proclin 300.

The invention also provides an in vitro diagnostic kit for the HPV type 16 E7 oncoprotein detection, which includes:
  a microplate coated with an HPV type 16 E7 antibody, wherein the coating amount of the antibody in each microwell of the microplate is 0.05-0.5 µg;
  and an HRP-labeled HPV type 16 E7 antibody with the concentration of 0.05-0.4 µg/ml.

Furthermore, the kit also includes human cervical exfoliated lysis buffer.

Preferably, the human cervical exfoliated lysis buffer includes 0.05%-1% (vol/vol) of surfactant, 10 mM-1M of buffer and 1 mM-10 mM of protease inhibitor. A more ideal lysis effect can be achieved by combining multiple freezing-thawing.

More preferably, the surfactant is one or more of Tween 20, Triton-100 or sodium dodecylsulfonate. The buffer is phosphate-buffered saline, Tris-HCl or a carbonate solution, and the protease inhibitor is one or more of cystatin, PMSF or Antipain.

More preferably, the human cervical exfoliated lysis buffer is prepared as follows: preparing 0.05%-1% (vol/vol) of surfactant with 10 mM-1M of buffer; and adding the protease inhibitor with final concentration of 1 mM-10 mM before use. More preferably, the human cervical exfoliated lysis buffer is prepared by a method comprising the following steps: preparing 1% of Tween 20 with 50 mM of PBS; and adding the protease inhibitor PMSF with final concentration of 5 mM before use.

Furthermore, the method for preparing the microplate coated with the HPV type 16 E7 antibody includes the following steps of taking an HPV type 16 E7 antibody, adding a coating buffer to the wells at an amount of 100 μl/well and standing at 4° C. overnight (16-18 h); washing with washing solution five times at an amount of 300 μl/well; adding blocking solution to the wells at an amount of 300 μl/well, and standing at 37° C. for 1-2 h for blocking; suction-drying in a drying room (18-26° C.) and sealing in vacuum (2-8° C.) to obtain a microwell plate coated with the HPV type 16 E7 antibody, and drying and storing, wherein the coating buffer is prepared by adding 0.5-5 mg of antibody to 1000 ml of buffer, and the buffer includes 1.59 g/L of $Na_2CO_3$ and 2.93 g/L of $NaHCO_3$; the washing solution includes 1.44 g/L of $Na_2HPO_4$, 0.24 g/L of $KH_2PO_4$, 8 g/L of NaCl, 0.2 g/L of KCl, 0.5 ml/L of Tween-20, and 0.3 ml/L of Proclin 300; and the blocking solution includes 1.44 g/L of $Na_2HPO_4$, 0.24 g/L of $KH_2PO_4$, 8 g/L of NaCl, 0.2 g/L of KCl, 10 g/L of BAS, 25 g/L of sucrose and 0.3 ml/L of Proclin 300.

Particularly, the kit includes the following main ingredients:
① the microplate pre-coated with the HPV type 16 E7 antibody, wherein the amount of the antibody in each microwell is 0.05-0.5 μg, and the microplate is a bar-shaped microwell plate (12 bar×8 wells) and arranged in a frame;
② the HPV type 16 E7 oncoprotein detection calibrators 0, 1, 2, 3, 4 and 5, wherein the freeze-dried powder serves as the calibrators, 1 ml dd$H_2O$ is respectively added for dissolving, and the linear concentration of the calibrator solution is 0, 10, 20, 40, 80, and 160 ng/ml, respectively;
③ the HPV type 16 E7 oncoprotein detection quality control samples 1 and 2, wherein the freeze-dried powder serves as the quality control samples, 1 ml dd$H_2O$ is added respectively for dissolving, and the concentration is 10 and 80 ng/ml, respectively;
④ the HRP-labeled HPV type 16 E7 antibody, which is directly used, and has the concentration of 0.05-0.4 μg/ml, one bottle and 12 ml per bottle
⑤ the human cervical exfoliated lysis buffer;
⑥ substrate solution: for example, chemiluminescent substrate solution (including substrate A and B solution) from Huzhou innoreagents Technology Co., Ltd. can be selected.
⑦ concentrated washing solution (20×): the concentrated washing solution contains a detergent and a preservative, and is diluted by 20 times with dd$H_2O$;
⑧ the sealing film: a viscous film for sealing the microwell plate during incubation.

The invention also provides a preparation method of the kit, comprising the following steps:
① preparing the microplate coated with the HPV type 16 E7 antibody
taking the HPV type 16 E7 antibody, adding a coating buffer to the wells at an amount of 100 μl/well and standing at 4° C. overnight (16-18 h); washing with washing solution five times at an amount of 300 μl/well; adding blocking solution to the wells at an amount of 300 μl/well, and standing at 37° C. for 1-2 h for blocking; suction-drying in a drying room (18-26° C.) and sealing in vacuum (2-8° C.) to obtain a microwell plate coated with the HPV type 16 E7 antibody, and drying and storing, wherein the coating buffer is prepared by adding 0.5-5 mg of antibody to 1000 ml of buffer, and the buffer includes 1.59 g/L of $Na_2CO_3$ and 2.93 g/L of $NaHCO_3$; the washing solution includes 1.44 g/L of $Na_2HPO_4$, 0.24 g/L of $KH_2PO_4$, 8 g/L of NaCl, 0.2 g/L of KCl, 0.5 ml/L of Tween-20, and 0.3 ml/L of Proclin 300; the blocking solution includes 1.44 g/L of $Na_2HPO_4$, 0.24 g/L of $KH_2PO_4$, 8 g/L of NaCl, 0.2 g/L of KCl, 10 g/L of BAS, 25 g/L of sucrose and 0.3 ml/L of Proclin 300;
② preparing calibrators and quality control samples
preparing the HPV type 16 E7 oncoprotein detection calibrators 0, 1, 2, 3, 4 and 5: taking lyophilized powder as the calibrators, and respectively adding 1 ml dd$H_2O$ for dissolving, wherein the linear concentration of the calibrator solution is 0, 10, 20, 40, 80, and 160 ng/ml, respectively;
preparing the HPV type 16 E7 oncoprotein detection quality control samples 1 and 2: taking lyophilized powder as the quality control samples, and respectively adding 1 ml dd$H_2O$ for dissolving, wherein the concentration is 10 and 80 ng/ml, respectively;
③ preparing the HRP-labeled HPV type 16 E7 antibody labeling with a sodium periodate method, adding an HRP stabilizer, mixing thoroughly and storing at 2-8° C., wherein the concentration is 0.05-0.4 μg/ml;
④ preparing the human cervical exfoliated lysis buffer
preparing 0.05%-1% (vol/vol) of surfactant with 10 mM-1M of buffer; and adding the protease inhibitor with final concentration of 1 mM-10 mM before use;
wherein the surfactant is one or more of Tween 20, Triton-100 or sodium dodecylsulfonate; the buffer is phosphate-buffered saline, Tris-HCl or a carbonate solution, and the protease inhibitor is one or more of cystatin, PMSF or Antipain;
⑤ preparing concentrated washing solution (20×)
adding 28.8 g of $Na_2HPO_4.12H_2O$, 4.8 g of $KH_2PO_4$, 160 g of NaCl, 4 g of KCl, 10 ml of Tween-20, and 6 ml of Proclin 300 to dd$H_2O$, diluting to 1000 ml, mixing thoroughly and storing at room temperature;
⑥ directly obtaining the commercially available substrate solution and sealing film by purchasing.

A detection method using the kit includes the following steps:
obtaining sufficient amount of human cervical exfoliated cells, vortex for 2-10 min, freezing-thawing in a −20° C. refrigerator for 1-3 times, shaking for 2-10 min, centrifuging for 10-30 min (13,000 rpm), and collecting supernatant for direct detection;

① taking the required pre-coated microplate from a 4° C. refrigerator and standing at room temperature for 15 min;

② adding 100 μl calibrator/quality control sample/sample to each well, mixing thoroughly and incubating at 37° C. for 30-60 min;

③ Remove the liquid from each well, adding 300 μl of washing solution to each well, standing and incubating for 1 min, remove the liquid from each well, drying by clapping on the absorbent paper, and repeating for 3-5 times;

④ adding 100 μl of HRP-labeled antibody solution to each well and standing and incubating at 37° C. for 30-60 min;

⑤ Remove the liquid from each well, adding 300 μl of washing solution to each well, standing and incubating for 1 min, remove the liquid from each well, drying by clapping on the absorbent paper, and repeating for 3-5 times;

⑥ adding 50 μl of chemiluminescent substrate A solution and 50 μl of chemiluminescent substrate B solution (Huzhou innoreagents Technology Co., Ltd.) into each well, placing in the chemiluminescence reader and reading the luminescence value;

obtaining a standard curve equation by taking the calibrator concentration as the abscissa and the luminescence value as the ordinate and by adopting the four-parameter logic fitting method, and calculating the HPV type 16 E7 oncoprotein concentration in the to-be-detected sample according to the standard curve equation.

| Result interpretation of the kit | |
|---|---|
| the HPV16 E7 protein concentration in cervical exfoliated cell samples | (ng/ml) |
| Negative | <15.02 |
| Positive | >15.02 |

The invention has the following beneficial effects:

Some clinical patients are infected with human papillomavirus (HPV), but the associated oncogene is low in expression or not expressed. In this case, the human papillomavirus (HPV) can be eliminated by the patient own immune system, without causing panic and unnecessary treatment, thereby reducing patient mental stress and economic stress. On the basis, the in vitro diagnostic kit is used for directly detecting the expression of high-risk HPV-associated oncoprotein and the expression level, and thus has a clear judgment on the infection degree of high-risk HPV, and facilitates subsequent treatment. The kit is complementary to the current gene level detection method, so that the test result is more accurate, the treatment program becomes clearer, and the patient is recovered soon. At the same tinge, the method requires only conventional chemiluminescence reader, which is inexpensive and can be used as the preferred method for cervical cancer screening.

BRIEF DESCRIPTION OF THE SEVERAL VIEWS OF THE DRAWINGS

FIG. 1 is the standard curve equation obtained by taking the calibrator concentration in the Embodiment 4 as the abscissa and the luminescence value as the ordinate and by adopting the four-parameter logic fitting method.

DETAILED DESCRIPTION OF THE INVENTION

The invention will be described in further detail with reference to the embodiments, but the embodiments are not intended to limit the scope of the invention.

Embodiment 1

A method for preparing the microplate coated with the HPV type 16 E7 antibody includes the following steps:

taking the HPV type 16 E7 antibody, adding a coating buffer to the wells at an amount of 100 μl/well and standing at 4° C. overnight (18 h); washing with washing solution five times at an amount of 300 μl/well; adding blocking solution to the wells at an amount of 300 μl/well, and standing at 37° C. for 2 h for blocking; suction-drying in a drying room (26° C.) and sealing in vacuum (4° C.) to obtain a microwell plate coated with the HPV type 16 E7 antibody, and drying and storing, wherein the coating buffer is prepared by adding 5 mg of antibody to 1000 ml of buffer, and the buffer includes 1.59 g/L of $Na_2CO_3$ and 2.93 g/L of $NaHCO_3$; the washing solution includes 1.44 g/L of $Na_2HPO_4$, 0.24 g/L of $KH_2PO_4$, 8 g/L of NaCl, 0.2 g/L of KCl, 0.5 ml/L of Tween-20, and 0.3 ml/L of Proclin 300; the blocking solution includes 1.44 g/L of $Na_2HPO_4$, 0.24 g/L of $KH_2PO_4$, 8 g/L of NaCl, 0.2 g/L of KCl, 10 g/L of BAS, 25 g/L of sucrose and 0.3 ml/L of Proclin 300;

Embodiment 2. Preparation of the Human Cervical Exfoliated Lysis Buffer and Lysate preparing 1% of Tween 20 with 50 mM of PBS; and adding the protease inhibitor PMSF with final concentration of 5 mM before use. 500 μl of lysate was added into a cervix exfoliated cell collection tube, the collection tube was vortex-shaken for 2 min, placed in a −20° C. freezer for 10 min, then placed in a 37° C. oven for 2 min, shaken again, and centrifuged (20 min, 13,000 rpm, 4° C.), and the supernatant was collected and detected.

Embodiment 3

A Preparation Method of the In Vitro Diagnostic Kit for the HPV Type 16 E7 Oncoprotein Detection ① preparation of the microplate pre-coated with the HPV type 16 E7 antibody, wherein the amount of the antibody in each microwell was 0.5 μg, and the microplate was a bar-shaped microwell plate (12 bars×8 wells) and arranged in a frame; and the preparation method was the same as the Embodiment 1;

② preparation of the HPV type 16 E7 oncoprotein detection calibrators 0, 1, 2, 3, 4 and 5, wherein the freeze-dried powder served as the calibrators, 1 ml $ddH_2O$ was respectively added for dissolving, and the linear concentration of the calibrator solution was 0, 10, 20, 40, 80, and 160 ng/ml, respectively;

③ preparation of the HPV type 16 E7 oncoprotein quality control samples 1 and 2, wherein the lyophilized powder served as the quality control samples, 1 ml $ddH_2O$ was respectively added for dissolving, and the concentration was 10 and 80 ng/ml, respectively;

④ preparation of the HRP-labeled HPV type 1.6 E7 antibody: labeling with the sodium periodate method, adding an HRP stabilizer, mixing thoroughly and storing at 2-8° C., wherein the concentration is 0.4 μg/ml, one bottle and 12 ml per bottle;

⑤ preparation of the human cervical exfoliated lysis buffer wherein the preparation method was the same as the Embodiment 2;

⑥ preparation of the substrate solution: chemiluminescent substrate A and B (Huzhou innoreagents Technology Co., Ltd.);

⑦ preparation of the concentrated washing solution (20×): adding 28.8 g of $Na_2HPO_4.12H_2O$, 4.8 g of $KH_2PO_4$, 160 g of NaCl, 4 g of KCl, 10 ml of Tween-20, and 6 ml of Proclin 300 to $ddH_2O$, diluting to 1000 ml, mixing thoroughly and storing at room temperature;

⑧ selection of the sealing film, wherein the sealing film was a viscous film for sealing the micro ell plate during incubation.

Embodiment 4. Detection of One Cervical Sample

The of the microplate and the lysis of the cervical sample were the same as the Embodiments 1-2. The detection was performed by (1) taking the required pre-coated microplate from the 4° C. refrigerator and standing at room temperature for 15 min. (2) Adding 100 μl calibrator/quality control sample/sample to each well, mixing thoroughly and incubating at 37° C. for 60 min. (3) Remove liquid from each well, adding 300 μl of washing solution to each well, standing and incubating for 1 min, the Remove liquid from each well, drying by clapping on the absorbent paper, and repeating for 5 times. (4) Adding 100 μl of HRP-labeled antibody solution to each well and standing and incubating at 37° C. for 60 min. (5) Remove liquid from each well, adding 300 μl of washing solution to each well, standing and incubating for 1 min, remove liquid from each well, drying by clapping on the absorbent paper, and repeating for 5 times. (6) Adding 50 μl of chemiluminescent substrate A and 50 μl of chemiluminescent substrate B into each well, placing in the chemiluminescence reader and reading the luminescence value; obtaining the standard curve equation by taking the calibrator concentration as the abscissa and the luminescence value as the ordinate and by adopting the four-parameter logic fitting method, which is shown in FIG. 1. The HPV type 16 E7 oncoprotein concentration in the to-be-detected sample was calculated to be 109.42 ng/ml according to the standard curve equation. According to the result interpretation, the sample is positive, and the patient needs positive treatment.

| ID | antigen concentration (ng/ml) | luminescence value | concentration calculated according to the standard curve (ng/ml) |
|---|---|---|---|
| Cal0 | 0 | 1060 | |
| Cal1 | 10 | 6912 | |
| Cal2 | 20 | 10721 | |
| Cal3 | 40 | 22244 | |
| Cal4 | 80 | 44363 | |
| Cal5 | 160 | 68556 | |
| sample to be detected | | 55124 | 109.42 |

The cervical exfoliated cells of a part of sample patient were detected by using the kit of the invention (for example the in vitro diagnostic kit of the Embodiment 3), and the detection data results are shown below:

TABLE 1 detection data results of the cervical exfoliated cells of sample patient

| sample number | HPV16 E7 antigen detection concentration (ng/ml) |
|---|---|
| No. 1 sample patient | 1.17 |
| No. 2 sample patient | 3.01 |
| No. 3 sample patient | 4.43 |
| No. 4 sample patient | 8.04 |
| No. 5 sample patient | 8.26 |
| No. 6 sample patient | 0.66 |
| No. 7 sample patient | 19.26 |
| No. 8 sample patient | 3.62 |
| No. 9 sample patient | 0.03 |
| No. 10 sample patient | 1.24 |
| No. 11 sample patient | 4.89 |
| No. 12 sample patient | 0.04 |
| No. 13 sample patient | 10.22 |
| No. 14 sample patient | 1.51 |
| No. 15 sample patient | 1.69 |
| No. 16 sample patient | 0.43 |
| No. 17 sample patient | 13.38 |
| No. 18 sample patient | 0.05 |
| No. 19 sample patient | 2.54 |
| No. 20 sample patient | 0.04 |
| No. 21 sample patient | 16.99 |
| No. 22 sample patient | 0.03 |
| No. 23 sample patient | 0.07 |
| No. 24 sample patient | 1.16 |
| No. 25 sample patient | 0.26 |
| No. 26 sample patient | 0.08 |
| No. 27 sample patient | 0.10 |
| No. 28 sample patient | 9.99 |
| No. 29 sample patient | 0.09 |
| No. 30 sample patient | 0.59 |
| No. 31 sample patient | 1.92 |
| No. 32 sample patient | 0.52 |
| No. 33 sample patient | 13.50 |
| No. 34 sample patient | 14.18 |
| No. 35 sample patient | 4.20 |
| No. 36 sample patient | 3.50 |
| No. 37 sample patient | 0.41 |
| No. 38 sample patient | 1.17 |
| No. 39 sample patient | 0.09 |
| No. 40 sample patient | 0.04 |
| No. 41 sample patient | 0.06 |
| No. 42 sample patient | 0.63 |
| No. 43 sample patient | 1.11 |
| No. 44 sample patient | 3.79 |
| No. 45 sample patient | 23.80 |
| No. 46 sample patient | 0.91 |
| No. 47 sample patient | 21.73 |
| No. 48 sample patient | 9.30 |
| No. 49 sample patient | 6.42 |
| No. 50 sample patient | 17.58 |
| No. 51 sample patient | 0.15 |
| No. 52 sample patient | 2.97 |
| No. 53 sample patient | 12.61 |
| No. 54 sample patient | 0.15 |
| No. 55 sample patient | 2.74 |
| No. 56 sample patient | 5.18 |
| No. 57 sample patient | 0.24 |
| No. 58 sample patient | 0.30 |
| No. 59 sample patient | 8.16 |
| No. 60 sample patient | 0.03 |
| No. 61 sample patient | 2.56 |
| No. 62 sample patient | 1.05 |
| No. 63 sample patient | 0.37 |
| No. 64 sample patient | 0.57 |
| No. 65 sample patient | 0.32 |
| No. 66 sample patient | 0.40 |
| No. 67 sample patient | 1.60 |

TABLE 1-continued detection data results of the cervical exfoliated cells of sample patient

| sample number | HPV16 E7 antigen detection concentration (ng/ml) |
|---|---|
| No. 68 sample patient | 0.25 |
| No. 69 sample patient | 3.89 |
| No. 70 sample patient | 0.17 |
| No. 71 sample patient | 5.23 |
| No. 72 sample patient | 1.93 |
| No. 73 sample patient | 3.70 |
| No. 74 sample patient | 0.99 |
| No. 75 sample patient | 0.91 |
| No. 76 sample patient | 1.15 |
| No. 77 sample patient | 1.29 |
| No. 78 sample patient | 10.33 |
| No. 79 sample patient | 8.46 |
| No. 80 sample patient | 6.06 |
| No. 81 sample patient | 9.76 |
| No. 82 sample patient | 2.66 |
| No. 83 sample patient | 2.25 |

TABLE 2

Detection data results of the cervical exfoliated cells of patients

| sample number | pathological data | HPV16 E7 antigen detection concentration (ng/ml) |
|---|---|---|
| No. 1 patient | squamous carcinoma of the cervix | 125.03 |
| No. 2 patient | CIN II | 82.46 |
| No. 3 patient | CIN III | 26.85 |
| No. 4 patient | squamous carcinoma of the cervix | 152.50 |
| No. 5 patient | CIN III | 45.98 |
| No. 6 patient | CIN II | 52.20 |
| No. 7 patient | CIN I | 19.19 |
| No. 8 patient | CIN II | 15.25 |
| No. 9 patient | CIN I | 1.89 |
| No. 10 patient | CIN II | 92.15 |
| No. 11 patient | CIN II | 19.45 |
| No. 12 patient | CIN III | 12.64 |
| No. 13 patient | CIN I | 16.85 |
| No. 14 patient | squamous carcinoma of the cervix | 112.05 |
| No. 15 patient | CIN I | 2.43 |
| No. 16 patient | CIN II | 62.20 |
| No. 17 patient | CIN III | 102.54 |
| No. 18 patient | CIN III | 75.25 |
| No. 19 patient | CIN II | 8.56 |

Data Analysis

1. According to the detection values of the sample patient, the average value, the standard deviation, and the Cutoff value were calculated. The detection results of cervical exfoliated cells of 83 cases of sample patient were averaged, and the standard variance SD was calculated. When the Cutoff value of the kit was determined, the sum of the average value of the sample patient and twice of the standard variance was selected as the judgment standard of the negative and positive expression of the HPV16 E7 protein, and the results are as follows:

The calculation formula of Cutoff is cutoff=average value+2*SD standard variance

TABLE 3 statistics of detection data table 1

| average value | 4.06 |
|---|---|
| SD standard variance | 5.48 |
| Cutoff | 15.02 ng/ml |

2. The negative and positive expression of the HPV16 E7 protein is determined by the Cutoff value, and the expression is considered to be positive when exceeding the Cutoff value, namely the HPV16 E7 protein is expressed, as compared with the pathological data.

3. Diagnosis results of the cervical exfoliated cells of the patients in Table 2, judged according to the Cutoff value ("+" shows that the test results are positive; "−" shows that the test results are negative)

| sample number | pathological data | HPV16 E7 antigen detection concentration (ng/ml) | judgement according to the Cutoff value negativity and positivity |
|---|---|---|---|
| No. 1 patient | cervical cancer | 125.03 | + |
| No. 2 patient | CIN III | 82.46 | + |
| No. 3 patient | CIN II | 26.85 | + |
| No. 4 patient | cervical cancer | 152.50 | + |
| No. 5 patient | CIN III | 45.98 | + |
| No. 6 patient | CIN II | 52.20 | + |
| No. 7 patient | CIN I | 19.19 | + |
| No. 8 patient | CIN II | 15.25 | + |
| No. 9 patient | CIN I | 1.89 | − |
| No. 10 patient | CIN II | 92.15 | + |
| No. 11 patient | CIN II | 19.45 | + |
| No. 12 patient | CIN III | 12.64 | − |
| No. 13 patient | CIN I | 16.85 | + |
| No. 14 patient | cervical cancer | 112.05 | + |
| No. 15 patient | CIN I | 2.43 | − |
| No. 16 patient | CIN II | 62.20 | + |
| No. 17 patient | CIN III | 102.54 | + |
| No. 18 patient | CIN III | 75.25 | + |
| No. 19 patient | CIN II | 8.56 | − |

Accuracy ratio formulated according to the diagnosis result positivity and negativity of the cervical exfoliated cells of the patients

| pathological data result | number of people | detection of HPV16 E7 protein | |
|---|---|---|---|
| | | positivity | negativity |
| CIN I | 4 | 2 (50%) | 2 |
| CIN II | 7 | 6 (85.7%) | 1 |
| CIN III | 5 | 4 (80%) | 1 |
| cervical cancer | 3 | 3 (100%) | 0 |
| | 19 | 15 (78.9%) | 4 |

As shown in Table 2, in the experiment, the total number of the detected patient cervical exfoliated cells is 19 cases, the detection results of 14 cases using the kit for the HPV16

E7 protein are positive, and the diagnostic sensitivity is up to 78.9%, in which the diagnostic sensitivity is up to 80% for the case samples of CIN II or above.

What is claimed is:

1. A method for preparing a microplate for a human papillomavirus (HPV) type 16 E7 oncoprotein detection, wherein the microplate is pre-coated with an HPV type 16 E7 antibody, wherein the amount of the HPV type 16 E7 antibody in each microwell of the microplate is 0.5 μg, the method consists of:
   adding a coating buffer to microwells at an amount of 100 μl/microwell and standing at 4° C. overnight (16-18 h);
   washing the microwells with a washing solution five times at an amount of 300 μl/microwell;
   adding a blocking solution to the microwells at an amount of 300 μl/microwell, and standing at 37° C. for 1-2 h for blocking;
   suction-drying in a drying room (18-26° C.) and sealing in vacuum (2-8° C.) to obtain a microplate coated with the HPV type 16 E7 antibody, and drying and storing,
   wherein the coating buffer is prepared by adding 5 mg of HPV type 16 E7 antibody to 1000 ml of buffer, and the buffer consists of 1.59 g/L of $Na_2CO_3$ and 2.93 g/L of $NaHCO_3$; the washing solution consists of 1.44 g/L of $Na_2HPO_4$, 0.24 g/L of $KH_2PO_4$, 8 g/L of NaCl, 0.2 g/L of KCl, 0.5 ml/L of Tween-20, and 0.3 ml/L of Proclin 300; the blocking solution consists of 1.44 g/L of $Na_2HPO_4$, 0.24 g/L of $KH_2PO_4$, 8 g/L of NaCl, 0.2 g/L of KCl, 10 g/L of bovine serum albumin (BSA), 25 g/L of sucrose and 0.3 ml/L of Proclin 300.

2. An in vitro diagnostic kit for HPV type 16 E7 oncoprotein detection, comprising:
   a microplate pre-coated with an HPV type 16 E7 antibody, wherein an amount of the HPV type 16 E7 antibody in each microwell of the microplate is 0.05-0.5 μg; and
   an HRP-labeled HPV type 16 E7 antibody with a concentration of 0.05-0.4 μg/ml,
   a human cervical exfoliated cell lysis buffer, wherein the human cervical exfoliated lysis buffer consists of 0.05%-1% of surfactant, 10 mM-1M of buffer and 1 mM-10 mM of protease inhibitor, and
   the surfactant is one or more of Tween 20, Triton-100 or sodium dodecylsulfonate, the buffer is phosphate-buffered saline, Tris-HCl or a carbonate solution, and the protease inhibitor is one or more of cystatin, PMSF or Antipain;
   wherein the microplate pre-coated with an HPV type 16 E7 antibody is prepared by a method consisting of the following steps:
   adding a coating buffer to the microwells at an amount of 100 μl/microwell and standing at 4° C. overnight (16-18 h);
   washing the microwells with a washing solution five times at an amount of 300 μl/microwell;
   adding a blocking solution to the microwells at an amount of 300 μl/microwell, and standing at 37° C. for 1-2 h for blocking;
   suction-drying in a drying room (18-26° C.) and sealing in vacuum (2-8° C.) to obtain a microplate coated with the HPV type 16 E7 antibody, and drying and storing,
   wherein the coating buffer is prepared by adding 0.5-5 mg of HPV type 16 E7 antibody to 1000 ml of buffer, and the buffer consists of 1.59 g/L of $Na_2CO_3$ and 2.93 g/L of $NaHCO_3$; the washing solution consists of 1.44 g/L of $Na_2HPO_4$, 0.24 g/L of $KH_2PO_4$, 8 g/L of NaCl, 0.2 g/L of KCl, 0.5 ml/L of Tween-20, and 0.3 ml/L of Proclin 300; the blocking solution consists of 1.44 g/L of $Na_2HPO_4$, 0.24 g/L of KH2PO4, 8 g/L of NaCl, 0.2 g/L of KCl, 10 g/L of BSA, 25 g/L of sucrose and 0.3 ml/L of Proclin 300.

3. A preparation method of an in vitro diagnostic kit for an HPV type 16 E7 oncoprotein detection, comprising:
   1) preparing a microplate pre-coated with an HPV type 16 E7 antibody which consists of
   adding a coating buffer to microwells at an amount of 100 μl/microwell and standing at 4° C. overnight (16-18 h);
   washing the microwells with a washing solution five times at an amount of 300 μl/microwell;
   adding a blocking solution to the microwells at an amount of 300 μl/microwell, and standing at 37° C. for 1-2 h for blocking;
   suction-drying in a drying room (18-26° C.) and sealing in vacuum (2-8° C.) to obtain a microplate coated with the HPV type 16 E7 antibody, and drying and storing,
   wherein the coating buffer is prepared by adding 0.5-5 mg of HPV type 16 E7 antibody to 1000 ml of buffer, and the buffer consists of 1.59 g/L of $Na_2CO_3$ and 2.93 g/L of $NaHCO_3$; the washing solution consists of 1.44 g/L of $Na_2HPO_4$, 0.24 g/L of $KH_2PO_4$, 8 g/L of NaCl, 0.2 g/L of KCl, 0.5 ml/L of Tween-20, and 0.3 ml/L of Proclin 300; the blocking solution consists of 1.44 g/L of $Na_2HPO_4$, 0.24 g/L of $KH_2PO_4$, 8 g/L of NaCl, 0.2 g/L of KCl, 10 g/L of BSA, 25 g/L of sucrose and 0.3 ml/L of Proclin 300;
   2) preparing calibrators and quality control samples which comprises
   preparing HPV type 16 E7 oncoprotein detection calibrators 0, 1, 2, 3, 4 and 5: taking lyophilized powder as the calibrators, and respectively adding 1 ml $ddH_2O$ for dissolving, wherein linear concentrations of calibrator solutions are 0, 10, 20, 40, 80, and 160 ng/ml, respectively;
   preparing HPV type 16 E7 oncoprotein detection quality control samples 1 and 2: taking lyophilized powder as the quality control samples, and respectively adding 1 ml $ddH_2O$ for dissolving, wherein concentrations are 10 and 80 ng/ml, respectively;
   3) preparing an HRP-labeled HPV type 16 E7 antibody which comprises
   labeling with a sodium periodate method, adding an HRP stabilizer, mixing thoroughly and storing at 2-8° C., wherein a concentration of the HRP-labeled HPV type 16 E7 antibody is 0.05-0.4 μm/ml;
   4) preparing a human cervical exfoliated lysis buffer which comprises
   preparing 0.05%-1% (vol/vol) of surfactant with 10 mM-1M of buffer and adding a protease inhibitor with final concentration of 1 mM-10 mM before use,
   wherein the surfactant is one or more of Tween 20, Triton-100 or sodium dodecylsulfonate; the buffer is phosphate-buffered saline, Tris-HCl or a carbonate solution, and the protease inhibitor is one or more of cystatin, PMSF or Antipain;
   5) preparing a concentrated washing solution (20×) which comprises adding 28.8 g of $Na_2HPO_4.12H_2O$, 4.8 g of $KH_2PO_4$, 160 g of NaCl, 4 g of KCl, 10 ml of Tween-20, and 6 ml of Proclin 300 to $ddH_2O$, diluting to 1000 ml, mixing thoroughly and storing at room temperature; and
   6) directly obtaining a substrate solution and a sealing film by purchasing.

* * * * *